United States Patent [19]

Hofmann-Igl

[11] 4,392,590

[45] Jul. 12, 1983

[54] EYE DROP DISPENSING BOTTLE

[75] Inventor: Ernest Hofmann-Igl, Kampen, Fed. Rep. of Germany

[73] Assignee: Basotherm GmbH, Biberach an der Riss, Fed. Rep. of Germany

[21] Appl. No.: 205,606

[22] Filed: Nov. 10, 1980

[30] Foreign Application Priority Data

Nov. 16, 1979 [DE] Fed. Rep. of Germany ....... 2946366

[51] Int. Cl.³ .............................................. A61M 1/00
[52] U.S. Cl. .................................. 222/174; 604/302; 222/215
[58] Field of Search ....................... 222/192, 215, 174; 128/233, 249

[56] References Cited

U.S. PATENT DOCUMENTS 2,911,128 11/1959 Krautkramer ................. 222/541 X
3,521,636 7/1970 Mahoney et al. ................... 128/233
3,598,121 8/1971 Lelicoff ........................... 128/249 X
3,934,590 1/1976 Campagna ....................... 128/249 X
4,002,168 1/1977 Petterson ........................ 128/249 X
4,134,403 1/1979 Johnson et al. ..................... 128/233

FOREIGN PATENT DOCUMENTS 1491774 5/1969 Fed. Rep. of Germany ...... 128/233

Primary Examiner—David A. Scherbel
Attorney, Agent, or Firm—Hammond & Littell, Weissenberger & Muserlian

[57] ABSTRACT

The invention provides an eye drop dispensing bottle, comprising, in addition to the dispensing opening, an elastic supporting finger by which the bottle may be supported, e.g. at the forehead over the eye, thus achieving an easy and accurate tilting of the dispensing opening in the direction towards the eye.

1 Claim, 2 Drawing Figures

U.S. Patent    Jul. 12, 1983    4,392,590

EYE DROP DISPENSING BOTTLE

The invention relates to an eye drop dispensing bottle.

The hitherto conventional bottles developed for this purpose have to be applied to the eye by an unsupported hand and, particularly with an unsteady hand, there arises the danger of injury as well as of misdirecting the eye drops. Moreover, as a rule, the second hand cannot be used for support as it is needed for keeping the eye open or lifting the eye-lid.

It is the object of the invention to provide an eye drop dispensing bottle by means of which the dispensing opening can be safely directed to the eye without the danger of injury.

This object is achieved by the fact that the supporting finger used here allows the bottle to be placed in a way that it gains support on the head, about which support the bottle may be slowly tilted for directing the dispensing opening to the eye.

At its free end the supporting finger should be as soft as possible in order that a certain pressure may be exerted free of pain when placing it, thereby ensuring preciser guidance. The required soft-elastical support may be achieved in particular by a predetermined bending in the principal direction, whereby a further bending is easily possible.

The invention is illustrated below in more detail in schematic drawings on the basis of several examples of embodiment.

Figure 1:
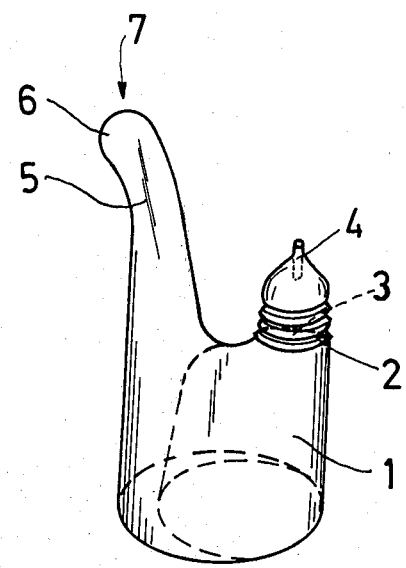
Figure 2:
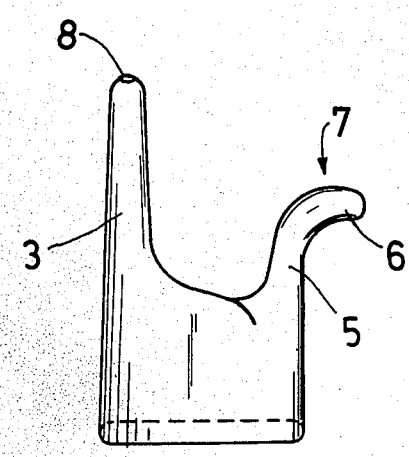

FIGS. 1 and 2 show diagrammatically two embodiments of a eye drop dispensing bottle according to the invention.

The eye drop dispensing bottle according to FIG. 1 has a body made of flexible plastic which in the horizontal plane has an approximately oval shape and comprises a bottle neck 2 on the upper side at one end of the oval, whose opening 3 can be capped by a droplet nozzle 4 serving as the dispensing opening. At the other end of the oval there is a soft-elastically yielding supporting finger 5. With this supporting finger the bottle is placed against the head—for instance in the area of the eyebrow—and is tilted about this supporting point, thus directing the droplet nozzle to the eye. By exerting side-pressure on the bottle the dispensing liquid can be dropped into the eye at precisely selected point without the nozzle touching the eye. The possibility of supporting the bottle allows accurate guidance even with an unsteady hand.

Preferably the supporting finger is bent away from the droplet nozzle at its free end 6 so that a soft supporting area 7 is formed. The supporting finger can form one piece with the body 1 and in this case it has to designed in a way that the bent end 6 is allowed to yield soft-elastically in the bending direction. However, the supporting finger can be a separate body—as shown by broken lines, e.g. consisting of foam-rubber, which is glued on afterwards.

In FIG. 2 the invention is demonstrated by a flat disposable eye drop dispensing bottle which can be produced e.g. by a blow molding process using a divided mold whose separating plane coincides with the longitudinal center plane of the bottle, or the like. In this case no conventional cap is provided for. Rather has the bottle neck 3 at its end to be provided with an opening 8, e.g. by piercing.

What I claim:

1. In an eye drop dispensing bottle made of elastically deformable plastic comprising a hollow body defining a cavity for containment of the product to be dispensed, a bottle neck extending upwardly from said hollow body and terminating in a dropping spout, said dropping spout and said bottle neck being in fluid communication with said hollow body, and a supporting finger extending upwardly from said hollow body and spaced from said bottle neck, the improvement which resides in that the supporting finger is made of soft-elastically yielding material, the upper end of said supporting finger is bent away from said bottle neck to form a soft, yielding supporting area, and the overall height of the supporting finger is less than the overall height of the bottle neck and dropping spout.

* * * * *